United States Patent
Baileykobayashi et al.

(10) Patent No.: US 10,046,022 B2
(45) Date of Patent: *Aug. 14, 2018

(54) SYNTHETIC PEPTIDE THAT INCREASES RADIOSENSITIVITY OF TUMOR CELLS AND USE OF SAME

(71) Applicant: TOAGOSEI CO., LTD., Tokyo (JP)

(72) Inventors: Nahoko Baileykobayashi, Tsukuba (JP); Noriko Usami, Tsukuba (JP); Tetsuhiko Yoshida, Tsukuba (JP)

(73) Assignee: TOAGOSEI CO. LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/164,073

(22) Filed: May 25, 2016

(65) Prior Publication Data

US 2016/0346346 A1 Dec. 1, 2016

(30) Foreign Application Priority Data

May 29, 2015 (JP) ................................ 2015-110910

(51) Int. Cl.
| | | |
|---|---|---|
| A61K 38/00 | (2006.01) | |
| A61K 38/08 | (2006.01) | |
| A61K 38/10 | (2006.01) | |
| A61K 41/00 | (2006.01) | |
| A61N 5/10 | (2006.01) | |
| A61K 9/16 | (2006.01) | |

(52) U.S. Cl.
CPC .............. *A61K 38/08* (2013.01); *A61K 38/10* (2013.01); *A61K 41/0038* (2013.01); *A61K 9/1623* (2013.01); *A61N 5/10* (2013.01); *A61N 2005/1087* (2013.01); *A61N 2005/1098* (2013.01)

(58) Field of Classification Search
CPC .. C07K 7/06; C07K 14/4703; C07K 2317/73; C07K 7/00; A61K 38/00
See application file for complete search history.

(56) References Cited

U.S. PATENT DOCUMENTS

| | | |
|---|---|---|
| 4,945,102 A | 7/1990 | Suzuki et al. |
| 2004/0034888 A1 | 2/2004 | Liu et al. |
| 2006/0122122 A1 | 6/2006 | Kobayashi et al. |
| 2010/0297758 A1 | 11/2010 | Yoshida et al. |
| 2012/0035112 A1 | 2/2012 | Yoshida et al. |
| 2012/0122210 A1 | 5/2012 | Yoshida et al. |
| 2013/0079273 A1 | 3/2013 | Yoshida et al. |
| 2015/0004697 A1 | 1/2015 | Kobayashi et al. |
| 2015/0018286 A1 | 1/2015 | Kobayashi et al. |
| 2015/0273018 A1 | 10/2015 | Kobayashi et al. |

FOREIGN PATENT DOCUMENTS

| | | |
|---|---|---|
| JP | H08-19111 B2 | 2/1996 |
| JP | 2668232 B2 | 10/1997 |
| JP | 5328357 B2 | 10/2013 |
| WO | 88/02366 A1 | 4/1988 |
| WO | 2007/048002 A2 | 4/2007 |
| WO | 2009/093692 A1 | 7/2009 |
| WO | 2010/106437 A1 | 9/2010 |
| WO | 2010/117079 A1 | 10/2010 |
| WO | 2011/152524 A1 | 12/2011 |
| WO | 2012/027282 A2 | 3/2012 |
| WO | 2013/094697 A1 | 6/2013 |
| WO | 2013/094698 A1 | 6/2013 |
| WO | 2014/061749 A1 | 4/2014 |
| WO | WO-2015064715 A1 * | 5/2015 ............... C07K 7/06 |

OTHER PUBLICATIONS

*Bradyrhizobium* sp. URHD0069, NCBI Reference Sequence: WP_029582671.1, Feb. 10, 2015, accessed on Sep. 6, 2017.*

Salisbury, Jeffrey L., et al., "Centrin-2 Is Required for Centriole Duplication in Mammalian Cells", Current Biology, vol. 12, 1287-1292, (2002).

Apr. 7, 2015 Written Opinion of the International Searching Authority issued in International Patent Application No. PCT/JP2014/084145.

Apr. 7, 2015 Search Report issued in Internatinal Patent Application No. PCT/JP2014/084145.

Gold, Leslie I. Calreticulin: non-endoplasmic reticulum functions in physiology and disease. FAESB J, vol. 24 (3), p. 665-83, Nov. 25, 2009.

Kepp, Oliver et al., "Viral subversion of immunogenic cell death". Cell cycle, vol. 8, No. 6, pp. 860-869, 2009.

Obeid, Michel et al., "Leveraging the Immune System during Chemotherapy: Moving Calreticulin to the Cell Surface Converts Apoptotic Death from the "Silent" to Immunogenic". Cancer Research, vol. 67, No. 17, pp. 7841-7944, 2007.

(Continued)

*Primary Examiner* — Hasan S Ahmed
*Assistant Examiner* — Kaipeen E Yang
(74) *Attorney, Agent, or Firm* — Oliff PLC (57) ABSTRACT

Provided are a synthetic peptide that increases the radiosensitivity of tumor cells and a pharmaceutical composition containing that synthetic peptide.

The peptide provided by the present invention is a synthetic peptide having a radiosensitizing peptide sequence including the following amino acid sequence:

$$CX_2X_3KX_5X_6X_7X_8C$$

(wherein, $X_2$ represents K or R, $X_3$ represents S or A, $X_5$ represents S or A, $X_6$ represents R or G, $X_7$ represents R or D and $X_8$ represents S or P); or, a modified amino acid sequence in which one, two or three amino acid residues are substituted, deleted and/or added in that amino acid sequence. In addition, the pharmaceutical composition provided by the present invention is a composition used to increase the sensitivity of tumor cells to radiation in tumor radiation therapy, and contains the synthetic peptide described above.

12 Claims, 2 Drawing Sheets

(56) References Cited

OTHER PUBLICATIONS

Marissal, Nathalie B. "Reduced Calreticulin Levels Link endoplasmic Reticulum Stress and Fas-Triggered Cell Death in Motoneurons Vulnerable to ALS". Journal of Neuroscience, vol. 32, No. 14, pp. 4901-4912, 2012.
Zhang, Ming et al., "Calreticulin-STAT3 Signaling Pathway Modulates Mitochondrial function in a Rat Model of Furazolidone-Induced Dialted Cardiomyopathy". Pios One, vol. 8, No. 6, pp. 66779, 2003.
Sep. 25, 2017 Office Action issued in U.S. Appl. No. 15/108,349.
Jun. 7, 2017 Office Action issued in U.S. Appl. No. 15/108,349.
Apr. 17, 2018 Office Action Issued in U.S. Appl. No. 15/108,349.

\* cited by examiner

SYNTHETIC PEPTIDE THAT INCREASES RADIOSENSITIVITY OF TUMOR CELLS AND USE OF SAME

BACKGROUND OF THE INVENTION

1. Field of the Invention

The present invention relates to a synthetic peptide that increases the radiosensitivity of tumor cells and to the use thereof. More particularly, the present invention relates to a pharmaceutical composition containing this synthetic peptide and the use of that pharmaceutical composition.

The present application claims priority on the basis of Japanese Patent Application No. 2015-110910, filed on May 29, 2015, the entire contents of which are incorporated herein by reference.

2. Description of the Related Art

Typical examples of methods used to treat tumors (and typically, malignant tumors or cancer) include surgical treatment, radiation therapy and chemotherapy. The methods used to treat these tumors (and typically, malignant tumors) are typically classified into local treatment, in which the site of tumor formation is treated locally, and systemic treatment, which targets the entire body of the patient (cancer patient) for treatment. Surgical treatment and radiation therapy are typical examples of local treatment for tumors, while chemotherapy is a typical example of systemic treatment for tumors.

Radiation therapy allows a tumor to be treated without surgery (resection). In addition, treating a tumor by combining surgical treatment and radiation therapy makes it possible to narrow the range of surgical resection in comparison with the case of treating the tumor by surgical treatment only. Namely, physical invasion accompanying surgical treatment (surgery) can be reduced by selecting radiation therapy (including cases of using in combination with surgical treatment). In addition, since it is also possible to preserve the organ where the tumor has formed (morphological preservation and functional preservation) as well as maintain aesthetics, it is highly useful to select radiation therapy (including cases of using in combination with surgical treatment).

In addition, radiation therapy is also characterized by enabling sites to be treated where surgery is difficult (i.e. it is possible to irradiate the site with radiation) and typically has less effect (adverse side effects) on the body in comparison with chemotherapy.

Radiation therapy refers to a method for controlling a tumor by utilizing the actions of radiation that inhibit cell growth and cause cell death. Since sensitivity to and reactivity with radiation differs between tumor cells and normal cells, cell proliferation by tumor cells can be inhibited and tumor cells can be caused to die by utilizing these differences in sensitivity and reactivity.

DNA can typically be damaged (cleaved) in cells irradiated with radiation. This is because cells in which DNA has been damaged tend to have difficulty in undergoing normal cell division. Namely, cell proliferation is inhibited as a result of cells dying due to being unable to carry out cell division or undergoing incomplete cell division, for example. In addition, cells in which DNA have been damaged may also die as a result of the DNA damage inducing apoptosis.

The Bergonie-Tribondeau law of radiosensitivity is known regarding sensitivity of cells to radiation, and in other words, states that the sensitivity to radiation of a cell increases as the frequency of cell division becomes higher, that sensitivity to radiation of a cell increases as the number of times that cell undergoes division in the future becomes higher, and that more morphologically and functionally undifferentiated cells exhibit higher sensitivity to radiation. In general, since there are many cases in which tumor cells match these characteristics in comparison with normal cells, they are more susceptible to the effects of radiation. In addition, tumor cells typically have a poorer function for repairing DNA damage caused by exposure to irradiation in comparison with normal cells. Thus, irradiating a tumor formation site with radiation makes it possible to inhibit the proliferation of tumor cells constituting the tumor and cause the tumor cells to die while minimizing the effects on normal cells present around the tumor.

SUMMARY OF THE INVENTION

However, the realization of effective radiation therapy is premised on the radiosensitivity of tumor cells being higher than that of normal cells. Namely, a large parameter used in radiation therapy referred to as the so-called therapeutic ratio (TR, wherein TR=normal tissue tolerance dose/tumor tissue control dose) is the premise for performing effective radiation therapy. Consequently, there are cases in which the therapeutic effect of radiation therapy may not be able to be adequately obtained depending on, for example, the tumor formation site, type of tumor, or tumor staging.

For example, the radiosensitivity of tumor cells may vary depending on such factors as the degree of differentiation of the tumor cells that constitute the tumor, the cell division cycle or enzyme concentration within the cells. More specifically, the radiosensitivity of tumor cells is considered to be higher in lowly differentiated tumor cells, tumor cells in the cell stage, and tumors cells having a high intracellular enzyme concentration.

In addition, radiosensitivity is also known to vary depending on the tissue. For example, tissue such as bone marrow or intestinal epithelium that demonstrates a high frequency of cell division tends to have higher radiosensitivity, while on the other hand, tissue such as nerve tissue or muscle tissue having a low frequency of cell division tends to have low radiosensitivity.

Consequently, in the case the difference in radiosensitivity between tumor cells and normal cells present around those tumor cells is small, namely in the case the previously described therapeutic ratio is small, it tends to be difficult to irradiate target cells at a radiation dose that is sufficient for controlling the proliferation of those cells.

Therefore, development has recently proceeded on drugs that increase the radiosensitivity of tumor cells (radiosensitizers). The concomitant use of these radiosensitizers with radiation therapy is expected to improve the therapeutic effect of radiation therapy. For example, treatment can be performed at a lower dose thereby making it possible to reduce damage to normal cells, and radiation therapy is expected to be able to be performed on tumors for which radiation therapy was previously not applicable.

Radiosensitizers in the form of chemical substances such as a 2-nitroimidazole derivative (Japanese Examined Patent Publication No. H8-19111), 1,2,4-benzotriazine oxide (Japanese Patent No. 2668232) or camptothecin (Japanese Patent No. 5328357) have been reported to be able to increase radiosensitivity of tumor cells. However, the majority of these radiosensitizers have yet to be used practically due to problems with adverse side effects and the like.

The development of drugs constituted of physiologically active peptides, which have a low molecular weight and in which the number of amino acid residues is relatively low, is expected for use as drugs (radiosensitizers) that increase the radiosensitivity of tumor cells as described above. Drugs constituted of physiologically active peptides are expected to reduce adverse side effects in comparison with radiosensitizers constituted of conventional chemical substances.

Therefore, the present invention was completed with the object of providing a composition (and typically, a pharmaceutical composition) capable of increasing radiosensitivity of tumor cells. More specifically, an object of the present invention is to provide a peptide capable of increasing radiosensitivity of tumor cells, and a composition (and typically, a pharmaceutical composition) for increasing radiosensitivity of at least one type of tumor cell that has that peptide as a component thereof.

The inventors of the present invention conducted extensive research on an artificially synthesizable, comparatively short chain-length peptide in order to achieve the object of increasing radiosensitivity of a target tumor cell. It was surprisingly found that, by supplying a peptide synthesized to contain any of the radiosensitizing peptide sequences disclosed herein to tumor cells, the radiosensitivity of the tumor cells was newly found to be able to increased, thereby leading to completion of the present invention. Any of the radiosensitizing peptide sequences disclosed herein are amino acid sequences that were completely unknown to be related to cell radiosensitivity, and the ability of these amino acid sequences to increase the radiosensitivity of tumor cells is a finding that was newly discovered by the inventors of the present invention.

According to the present invention, a composition having the composition indicated below is provided to realize the above object. Namely, one aspect of the composition disclosed herein is a pharmaceutical composition used to increase the sensitivity of tumor cells to radiation in tumor radiation therapy, including:

a synthetic peptide having a radiosensitizing peptide sequence including the following amino acid sequence:

(wherein, $X_2$ represents K or R, $X_3$ represents S or A, $X_5$ represents S or A, $X_6$ represents R or G, $X_7$ represents R or D and $X_8$ represents S or P); or, a modified amino acid sequence in which one, two or three amino acid residues are substituted, deleted and/or added in that amino acid sequence.

Typically, the pharmaceutical composition disclosed herein contains at least one type of pharmacologically acceptable vehicle (such as at least one type of base material that contributes to improved stability of the peptide or a liquid vehicle such as physiological saline or various types of buffers).

In the following description, the synthetic peptide having a radiosensitizing peptide sequence (namely, the synthetic peptide having radiosensitizing activity) is also referred to as a "radiosensitizing synthetic peptide".

The pharmaceutical composition contains a synthetic peptide having a radiosensitizing peptide sequence capable of increasing the sensitivity of tumor cells to radiation, or in other words, a radiosensitizing synthetic peptide. Consequently, the pharmaceutical composition can be preferably used as a composition (pharmaceutical composition) for increasing the radiosensitivity of tumor cells in tumor radiation therapy. Namely, the pharmaceutical composition can typically be used as an assistant (so-called radiosensitizer) in tumor radiation therapy.

The therapeutic effect on a tumor can be expected to be improved by performing tumor radiation therapy using the pharmaceutical composition having the composition described above. For example, tumor radiation therapy can be performed by irradiating with radiation at a lower dose than in the past as a result of improving the radiosensitivity of tumor cells. If the radiation dose per irradiation can be reduced, the number of times a tumor can be irradiated with radiation can be increased. In addition, in the case of a tumor for which it was previously difficult to perform adequate radiation therapy due to low radiosensitivity (and typically, a malignant tumor or cancer), improving the radiosensitivity of tumor cells constituting the tumor enables radiation therapy to be performed on that tumor.

In addition, since the total dose of radiation or radiation per dose radiated onto a tumor can be lowered, radiation damage to normal cells present around the tumor can be reduced. Namely, adverse side effects attributable to radiation therapy can be reduced.

In addition, since the radiosensitizing synthetic peptide described above is a synthetic peptide having a comparatively short chain length, it can easily be artificially produced. For example, it can be easily produced by production using chemical synthesis (or biosynthesis). In addition, since the radiosensitizing synthetic peptide is a synthetic peptide having a comparatively simple structure (typically in the form of a linear peptide chain), it can be handled easily. Consequently, it is preferable as an active ingredient of a composition used to increase the sensitivity of tumor cells to radiation (namely, a substance involved in increasing the radiosensitivity of tumor cells).

In a preferred embodiment of the pharmaceutical composition disclosed herein, the radiosensitizing peptide sequence is any of the following amino acid sequence:

(SEQ ID NO. 1)
CKSKSRRSC;

or, a modified amino acid sequence in which one, two or three amino acid residues are substituted, deleted or added in that amino acid sequence.

The amino acid sequence disclosed herein as SEQ ID NO. 1 is an amino acid sequence uniquely obtained by translating an RNA sequence constituting siRNA of human-derived centrin-2, and is highly capable of increasing the radiosensitivity of tumor cells. Consequently, it is preferable as a radiosensitive peptide sequence constituting the radiosensitizing peptide contained in the pharmaceutical composition disclosed herein.

In another preferred embodiment of the pharmaceutical composition disclosed herein, the synthetic peptide has a membrane-permeable peptide sequence on the N-terminal side or C-terminal side of the radiosensitizing peptide sequence.

This radiosensitizing synthetic peptide having this membrane-permeable peptide sequence is able to efficiently migrate from the outside of a target tumor cell (outside the cell membrane) to the inside of the tumor cells due to the function of the membrane-permeable peptide sequence. Consequently, the radiosensitivity of tumor cells can be efficiently increased, thereby making this preferable.

In addition, in another preferred embodiment of the present invention, the synthetic peptide has the following amino acid sequence for the membrane-permeable peptide sequence:

KKRTLRKNDRKKR. (SEQ ID NO. 2)

The amino acid sequence disclosed herein as SEQ ID NO. 2 is a typical example of an amino acid sequence constituting a membrane-permeable peptide, and can be preferably used to carry out the present invention.

In addition, in another preferred embodiment of the pharmaceutical composition disclosed herein, the total number of amino acid residues constituting the synthetic peptide is 30 or less.

A peptide constituted of such a short peptide chain has high configurational stability (in terms of for example, resistance to proteases) and superior storageability. Moreover, a peptide having such a short peptide chain is easy to synthesize chemically, and can be produced (acquired) at a comparatively inexpensive production cost. Consequently, this synthetic peptide is preferable as the active ingredient of the pharmaceutical composition disclosed herein (composition used to increase the sensitivity of tumor cells to radiation).

In addition, in another preferred embodiment of the pharmaceutical composition disclosed herein, the tumor cells are any of tumor cells constituting prostate cancer, cervical cancer, breast cancer, gallbladder cancer, pancreatic cancer, colon cancer, rectal cancer, kidney cancer, lung cancer, esophageal cancer, pharyngeal cancer, stomach cancer, melanoma (e.g. malignant melanoma), mesothelioma or sarcoma.

These tumor cells are typically cells that have low sensitivity to radiation (high resistance to radiation therapy). Consequently, use of the pharmaceutical composition disclosed herein (composition used to increase the sensitivity of tumor cells to radiation) on these tumor cells makes it possible to increase the radiosensitivity of these tumor cells. Namely, use of the pharmaceutical composition disclosed herein in radiation therapy for these tumors makes it possible to improve the therapeutic effect of radiation therapy.

In addition, in another preferred embodiment of the pharmaceutical composition disclosed herein, the radiation used in the radiation therapy is any of X-rays or electromagnetic waves having a wavelength shorter than that of X-rays, a proton beam or a heavy particle beam using ions having a mass equal to or greater than helium.

This radiation is a typical example of radiation used in tumor radiation therapy. The pharmaceutical composition disclosed herein (e.g. composition used to increase the sensitivity of tumor cells to radiation) is able to improve sensitivity to this radiation of at least one type of tumor cell.

In addition, in another preferred embodiment of the pharmaceutical composition disclosed herein, the radiation used in the radiation therapy is X-ray radiation. X-ray radiation is currently used most commonly in tumor radiation therapy. Consequently, devices for radiating X-rays are used comparatively commonly, thereby enabling treatment to be performed using existing equipment without having to invest large amounts for new radiation equipment.

In addition, in the case of irradiating a patient with X-rays from outside the body, the dose near the outer surface of the body is known to be the highest and then subsequently diminish as the X-rays penetrate inside the body. Consequently, in the case of treating a tumor located deep in the body, normal cells irradiated with X-rays that are present between the outer surface of the body and the area affected by a tumor tend to also be irradiated with high doses of X-rays. In addition, since X-rays that have irradiated the body have a superior ability of passing through the body, they penetrate into areas of the body that are deeper than the area affected by the tumor. Consequently, normal cells around the tumor tend to be susceptible to damage (in the form of inhibition of cell proliferation and cell death). In contrast, since the radiosensitivity of tumor cells is specifically increased by using the pharmaceutical composition disclosed herein, highly therapeutic effects can be expected even by irradiating with X-rays at a low dose. As a result, damage to normal cells present around tumor cells can be reduced. In addition, since the X-ray dose per irradiation is reduced, the number of times a tumor at the same site can be irradiated with X-rays can be increased, thereby making it possible to improve the therapeutic effect.

In addition, in another aspect thereof, the present invention provides a method for inhibiting the proliferation of at least one type of tumor cell in vitro or in vivo, including supplying a synthetic peptide that increases the radiosensitivity of target tumor cells to target cells, and irradiating the cells with radiation after supplying the peptide. Here, the synthetic peptide is a peptide having a radiosensitizing peptide sequence including the following amino acid sequence:

$CX_2X_3KX_5X_6X_7X_8C$ (wherein, $X_2$ represents K or R, $X_3$ represents S or A, $X_5$ represents S or A, $X_6$ represents R or G, $X_7$ represents R or D and $X_8$ represents S or P); or, a modified amino acid sequence in which one, two or three amino acid residues are substituted, deleted and/or added in that amino acid sequence (namely, the previously described radiosensitizing synthetic peptide). In addition, the radiation is any of X-rays or electromagnetic waves having a wavelength shorter than that of X-rays, a proton beam or a heavy particle beam using ions having a mass equal to or greater than helium.

According to this method for inhibiting proliferation of tumor cells, the radiosensitivity of target tumor cells can be increased by supplying the radiosensitizing peptide disclosed herein to the target tumor cells (such as by supplying to a medium in which the target tumor cells are cultured). As a result, according to this method for inhibiting proliferation of tumor cells, the proliferation of tumor cells can be inhibited remarkably in comparison with the case of irradiating tumor cells with radiation without supplying the radiosensitizing synthetic peptide. Namely, according to this method for inhibiting proliferation of tumor cells, the proliferation of tumor cells can be efficiently inhibited by a simple technique consisting of supplying the radiosensitizing synthetic peptide disclosed herein to target tumor cells and irradiating the tumor cells with radiation.

In addition, in another preferred embodiment of the method for inhibiting proliferation of tumor cells disclosed herein, the radiosensitizing peptide sequence is the following amino acid sequence:

CKSKSRRSC; (SEQ ID NO. 1)

or, a modified amino acid sequence in which one, two or three amino acid residues are substituted, deleted or added in that amino acid sequence.

The radiosensitizing synthetic peptide having this radiosensitizing peptide sequence is highly capable of increasing the radiosensitivity of tumor cells. Consequently, it can be preferably used in the method for inhibiting proliferation of tumor cells disclosed herein.

In addition, in another preferred embodiment of the method for inhibiting proliferation of tumor cells disclosed herein, the radiation is X-ray radiation.

According to the method for inhibiting proliferation of tumor cells disclosed herein, the proliferation of target tumor cells can be efficiently inhibited by irradiating the tumor cells with X-rays.

In addition, in another aspect thereof, the present invention provides a method for treating a tumor, including administering a synthetic peptide that increases the radiosensitivity of tumor cells to a patient, and irradiating the affected area of the tumor with radiation. Here, the synthetic peptide is a peptide having a radiosensitizing peptide sequence including the following amino acid sequence:

(wherein, $X_2$ represents K or R, $X_3$ represents S or A, $X_5$ represents S or A, $X_6$ represents R or G, $X_7$ represents R or D and $X_8$ represents S or P); or, a modified amino acid sequence in which one, two or three amino acid residues are substituted, deleted and/or added in that amino acid sequence. In addition, the radiation is any of X-rays or electromagnetic waves having a wavelength shorter than that of X-rays, a proton beam or a heavy particle beam using ions having a mass equal to or greater than helium.

According to this tumor treatment method, the radiosensitivity of tumor cells constituting the tumor can be increased by administering the radiosensitizing synthetic peptide disclosed herein to a patient (such as by administering by injection or oral administration). Consequently, tumor cells can be efficiently killed or the proliferation of tumor cells can be inhibited by subsequent irradiation. Namely, according to this tumor treatment method, effective tumor treatment can be realized. In addition, according to this tumor treatment method, a tumor can be treated by, for example, irradiating at a lower dose. As a result, the duration of irradiation can be extended or the number of times the tumor is irradiated can be increased, thereby making it possible to improve the efficacy of tumor treatment. In addition, since the total radiation dose radiated onto the affected area (namely, the body) or the radiation dose per irradiation, is lowered, damage to normal cells caused by irradiation can be reduced. As a result, adverse side effects associated with radiation therapy (so-called radiation damage such as musical damage, dermatitis or bone marrow suppression) can be inhibited.

DESCRIPTION OF THE PREFERRED EMBODIMENTS

The following provides a description of preferred embodiments of the present invention. Matters not specifically mentioned in the present specification (such as the primary structure and chain length of the synthetic peptide disclosed herein) that are required to carry out the present invention (such as general matters relating to the method used to chemically synthesize the peptide, cell culturing method, preparation of the pharmaceutical composition having the peptide as a component thereof, or radiation irradiation method) should be understood to constitute design matters of a person with ordinary skill in the art based on the prior art in the fields of cell engineering, physiology, medicine, pharmacology, organic chemistry, biochemistry, genetic engineering, protein engineering, molecular biology and genetics. The present invention can be carried out based on the contents disclosed in the present specification and common technical knowledge in the relevant fields. Furthermore, in the following explanation, amino acids, depending on the case, are represented using the single letter code in compliance with nomenclature relating to amino acids as indicated in the IUPAC-IUB guidelines (although the three letter code is used to represent amino acids in the sequence listings).

In addition, the contents of all literature cited in the present specification are incorporated in the present specification by reference.

In addition, in the present specification, a "synthetic peptide" refers to a peptide fragment for which the peptide chain thereof alone does not independently or stably exist in nature, is produced by artificial chemical synthesis or biosynthesis (namely, produced based on genetic engineering), and stably exists in a prescribed composition (such as a composition used to increase the radiosensitivity of tumor cells, e.g. a radiosensitizing composition).

In addition, in the present specification, "peptide" is a term indicating an amino acid polymer having a plurality of peptide bonds, and although is not subjected to limitations on the number of amino acid residues contained in the peptide chain, has a comparatively small molecular weight such that the total number of amino acid residues is typically about 100 or less (preferably 60 or less, and for example, 50 or less).

In addition, in the present specification, "amino acid residue", unless specifically indicated otherwise, is a term that includes N-terminal amino acids and C-terminal amino acids of a peptide chain.

Furthermore, amino acid sequences described in the present specification always have the N-terminal side on the left side and the C-terminal side on the right side.

A "modified amino acid sequence" as described with respect to a prescribed amino acid sequence in the present specification refers to an amino acid sequence formed by substituting, deleting and/or adding (inserting) from one to a plurality of amino acid residues, such as one, two or three amino acid residues, without impairing the function of the prescribed amino acid sequence (such as radiosensitizing activity possessed by the radiosensitizing synthetic peptide or membrane permeability possessed by a membrane-permeable peptide sequence to be subsequently described). For example, a sequence formed by so-called conservative amino acid replacement in which one, two or three amino acid residues are conservatively replaced (such as a sequence in which a basic amino acid residue is replaced with an acidic amino acid residue in the manner of mutual substitution of a lysine residue and arginine residue), or a sequence in which one, two or three amino acid residues are added (inserted) or deleted in a prescribed amino acid sequence, is a typical example included in a modified amino acid sequence as referred to in the present specification. Thus, in addition to synthetic peptides constituted of an amino acid sequence identical to an amino acid sequence of each of the sequence ID numbers, synthetic peptides constituted of amino acid sequences, in which one, two or three amino acid residues have been substituted (such as in the manner of the previously described conservative amino acid replacement), deleted and/or added in an amino acid sequence of each of the sequence ID numbers, and demonstrate similar radiosensitizing activity, are also included in the radiosensitizing synthetic peptide disclosed herein.

In the present specification, "tumor" is a term used in a broad context, and refers to tumors in general, including both benign tumors and malignant tumors (but typically referring to a malignant tumor). Namely, tumor includes carcinomas and sarcomas or lesions of the blood or hematopoietic tissue (such as leukemia or lymphoma). Furthermore, "cancer" refers to a "malignant tumor" included in the tumors described above, and also refers to an epithelial malignant tumor among the above tumors. In addition, "tumor cells" refer to cells that form a tumor. Typically, tumor cells refer to cells that have proliferated abnormally and independently of surrounding normal tissue (so-called cancerous cells). Thus, unless specifically defined otherwise, cells unrelated to the origin or properties of normal cells are referred to as tumor cells provided they are cells that are classified as tumor cells (and typically, cancer cells) and not normal cells. Cells constituting epithelial tumors (such as squamous cell carcinoma or adenoma), non-epithelial tumors (such as various types of sarcoma or osteosarcoma), various types of cytomas (such as neuroblastoma or retinoblastoma), lymphoma or melanoma and the like are included in tumor cells as referred to here.

In addition, in the present specification, "radiosensitivity" refers to the degree of susceptibility to the effects of radiation. Namely, increasing the radiosensitivity of cells refers to making the target cells more susceptible to the effects of radiation. Here, the effects of radiation refer to all effects on cells, tissue or the body, and examples thereof include damage to DNA, inhibition of cell proliferation, cell death and cell damage. Typical examples of the effects of radiation at the cellular level include inhibition of cell proliferation and cell death. Thus, the radiosensitivity of target cells can, for example, be determined according to the degree of the decrease in cell proliferation rate (cell survival rate) of the target cells attributable to irradiation. In addition, in the case of a solid tumor that proliferates in the form of a mass of cells in a specific organ or tissue and the like, radiosensitivity of the tumor can be determined according to the degree of the reduction in size of the tumor attributable to irradiation.

Although the radiosensitizing synthetic peptide disclosed herein typically has the ability to increase the radiosensitivity of tumor cells when supplied (such as administered into the body of a patient) to prescribed tumor cells (typically, cells derived from a human or mammal, bird or other non-human mammal) (and this ability is hereinafter referred to as "radiosensitizing activity"), this synthetic peptide was first discovered by the inventors of the present invention. Consequently, the proliferation of tumor cells, in which radiosensitivity has been increased as a result of supplying the radiosensitizing synthetic peptide, is easily inhibited by irradiation. Thus, normal cell proliferation of the tumor cells can be inhibited by irradiating tumor cells supplied with the radiosensitizing synthetic peptide with radiation, and as a result thereof, the tumor cells can be induced to die without proliferating. Namely, the radiosensitizing synthetic peptide disclosed herein is a synthetic peptide for which the ability to increase cell proliferation inhibitory effects on the tumor cells by irradiating with radiation when supplied to prescribed tumor cells was discovered by the inventors of the present invention.

In addition, according to the present invention, a composition (and typically, a pharmacological composition such as a pharmaceutical composition) is provided that is used to increase the radiosensitivity of at least one type of tumor cell, and contains as an active ingredient thereof (namely, a substance involved in increasing the radiosensitivity of target tumor cells) at least one type of the radiosensitizing synthetic peptide disclosed herein (to also be referred to as a "radiosensitizing composition"). Furthermore, the radiosensitizing composition (so-called radiosensitizer) can preferably be used as a pharmaceutical composition used to increase the radiosensitivity of tumor cells in tumor radiation therapy.

According to the radiosensitizing synthetic peptide (and radiosensitizing composition containing that peptide) disclosed herein, the radiosensitivity of tumor cells supplied with the radiosensitizing synthetic peptide (and radiosensitizing composition containing that peptide) can be specifically increased. As a result, the difference in radiosensitivity between tumor cells constituting a tumor and normal cells surrounding the tumor cells can be increased. Namely, a parameter used in radiation therapy referred to as the so-called therapeutic ratio (TR) (TR=normal tissue tolerance dose/tumor tissue control dose) can also be increased. This effect of increasing therapeutic ratio makes it possible to realize improvement of therapeutic effect and reduction of adverse side effects.

As has been described above, the radiosensitizing synthetic peptide disclosed herein is a synthetic peptide having a radiosensitizing peptide sequence that was newly discovered by the inventors of the present invention to have the ability to increase the radiosensitivity of target tumor cells (namely, radiosensitizing activity). More specifically, the radiosensitizing synthetic peptide has for the radiosensitizing peptide sequence thereof the following amino acid sequence:

$CX_2X_3KX_5X_6X_7X_8C$ (wherein, $X_2$ represents K or R, $X_3$ represents S or A, $X_5$ represents S or A, $X_6$ represents R or G, $X_7$ represents R or D and $X_8$ represents S or P); or, a modified amino acid sequence thereof.

Examples of preferable sequences of the radiosensitizing peptide include the following amino acid sequence:

(SEQ ID NO. 1)

CKSKSRRSC and modified amino acid sequences thereof. Alternatively, the following amino acid sequence:

CRAKAGDPC (SEQ ID NO. 8)

or a modified amino acid sequence thereof is also preferable for the radiosensitizing peptide sequence disclosed herein.

The specific amino acid sequence indicated in SEQ ID NO. 1 or SEQ ID NO. 8 is an artificial amino acid sequence of a total of 9 amino acid residues uniquely obtained by the inventors of the present invention by translating an RNA sequence constituting siRNA of human-derived centrin-2.

Here, centrin refers to a centrosome-associated protein involved in centrosome replication and microtubule cleavage as one of the composite proteins of centrosomes, and centrin-2 is one of the proteins belonging to the centrin family (more specifically, centrin-1, centrin-2, centrin-3 and the like) (refer to Current Biology, Vol. 12, 2002, pp. 1287-1292).

Alternatively, although the radiosensitizing synthetic peptide disclosed herein may be a peptide constituted only of the previously mentioned radiosensitizing peptide sequence, it can also be a synthetic peptide having a membrane-permeable peptide sequence on the N-terminal side or C-terminal side of the radiosensitizing peptide sequence. A synthetic peptide having a membrane-permeable peptide sequence enables the synthetic peptide to be rapidly introduced into target cells when supplied to the cells. As a result, radiosensitizing activity can be improved.

The membrane-permeable peptide sequence can be used without any particular limitations provided it is an amino acid sequence that constitutes a membrane-permeable peptide capable of passing through a cell membrane and/or nuclear membrane. Although numerous preferable membrane-permeable peptide sequences are known, an amino acid sequence (including modified amino acid sequences) associated with a nucleolar localization signal (NoLS) is particularly preferable for the amino acid sequence of a membrane-permeable peptide sequence of the radiosensitizing synthetic peptide. Preferable examples of the membrane-permeable peptide sequence associated with NoLS as well as other membrane-permeable peptide sequences (including modified amino acid sequences) are indicated with SEQ ID NOS. 2 to 6. The following provides a detailed description thereof.

Namely, the amino acid sequence of SEQ ID NO. 2 corresponds to an NoLS constituting a total of 13 amino acid residues from the 491st amino acid residue to the 503rd amino acid residue of LIM kinase-2, which is a type of protein kinase associated with intracellular signal transduction and is present in human endothelial cells.

The amino acid sequence of SEQ ID NO. 3 corresponds to an NoLS constituting a total of 8 amino acid residues contained in a nucleocapsid protein (N protein) of avian infectious bronchitis virus (IBV).

The amino acid sequence of SEQ ID NO. 4 corresponds to a membrane-permeable peptide sequence constituting a total of 11 amino acid residues derived from a protein transduction domain included in the TAT of human immunodeficiency virus (HIV).

The amino acid sequence of SEQ ID NO, 5 corresponds to a membrane-permeable peptide sequence constituting a total of 11 amino acid residues of a protein transduction domain (PTD4) obtained by modifying the above TAT.

The amino acid sequence of SEQ ID NO. 6 corresponds to a membrane-permeable peptide sequence constituting a total of 16 amino acid residues derived from the ANT of Antennapedia, a variant of *Drosophila*.

Furthermore, the membrane-permeable peptide sequences described above contained in the sequence listings are merely intended to be examples, and there are no limitations on the peptide sequence actually used. Various membrane-permeable peptide sequences able to be used to carry out the present invention are described in numerous literature published at the time of the filing date of the present application. The amino acid sequences of these membrane-permeable peptide sequences can be easily determined by an ordinary search means.

The amino acid sequence indicated in SEQ ID NO. 2, which is also described in WO 2009/093692 is particularly preferable for use as a membrane-permeable peptide sequence. Combining this amino acid sequence indicated in SEQ ID NO. 2 with one of the radiosensitizing peptide sequences previously described (such as the amino acid sequence indicated in SEQ ID NO. 1 or SEQ ID NO. 8) makes it possible to obtain a synthetic peptide that demonstrates a high level of radiosensitizing activity.

A preferred embodiment of the radiosensitizing synthetic peptide disclosed herein contains the following amino acid sequence: CKSKSRRSCGKKRTLRKNDRKKR (SEQ ID NO. 7). The amino acid sequence indicated in SEQ ID NO. 7 is an amino acid sequence constituting a total of 23 amino acid residues constructed by combining the amino acid sequence indicated in SEQ ID NO. 1 with the amino acid sequence derived from LIM kinase-2 indicated in SEQ ID NO. 2 through a single glycine residue (0) serving as a linker.

Several of the peptide chains (amino acid sequences) of the radiosensitizing synthetic peptide disclosed herein can be constructed by suitably combining a radiosensitizing peptide sequence as previously described with a membrane-permeable peptide sequence. Either the radiosensitizing peptide sequence or membrane-permeable peptide sequence may be relatively arranged on the C-terminal side (N-terminal side). In addition, the radiosensitizing peptide sequence and membrane-permeable peptide sequence are preferably arranged adjacent to each other. Namely, an amino acid residue not contained in either sequence moiety is either not present between the radiosensitizing peptide sequence and the membrane-permeable peptide sequence, or if present, the number of these amino acid residues is preferably about one to three. For example, one or a plurality (typically 2 or 3) amino acid residues (such as one or a plurality of glycine (G) residues) functioning as a linker can be contained between the radiosensitizing peptide sequence and membrane-permeable peptide sequence.

At least one of the amino acid residues of the radiosensitizing synthetic peptide disclosed herein is preferably amidated. Amidation of a carboxyl group of an amino acid residue (typically, the C-terminal amino acid residue) makes it possible to improve the structural stability (such as protease resistance) of the synthetic peptide.

The radiosensitizing synthetic peptide can also contain a sequence (amino acid residue) moiety other than the amino acid sequences that constitute the radiosensitizing peptide sequence and membrane-permeable peptide sequence provided radiosensitizing activity is not lost. Although there are no particular limitations thereon, the amino acid sequence is preferably a sequence that is able to maintain the three-dimensional shape (typically, a linear shape) of the radiosensitizing peptide sequence and membrane-permeable peptide sequence moiety. The total number of amino acid residues that constitute the peptide chain of the radiosensitizing synthetic peptide is suitably 100 or less, preferably 60 or less and more preferably 50 or less. For example, a synthetic peptide in which the total number of amino acid residues is 30 or less is particularly preferable.

Such peptides having a short chain length are easily chemically synthesized and allow the radiosensitizing synthetic peptide to be easily produced. Furthermore, although there are no particular limitations on the conformation of the peptide provided it demonstrates radiosensitizing activity that increases the radiosensitivity of tumor cells in the environment in which it is used (outside the body, and particularly in a medium used to culture the target cells), a linear or helical conformation is preferable from the viewpoint of making it difficult for the peptide to become an immunogen (antigen). A peptide having such a shape has difficulty in composing an epitope. From this viewpoint, a linear peptide is preferable for the radiosensitizing synthetic peptide used to increase the radiosensitivity of tumor cells, and the peptide also preferably has a comparatively low molecular weight (typically having a number of amino acid residues of 60 or less (and particularly 30 or less)).

Although there are no particular limitations on the ratio of the radiosensitizing peptide sequence and membrane-permeable peptide sequence to the entire amino acid sequence (namely, the percentage of the number of amino acid residues that constitute the radiosensitizing peptide sequence and membrane-permeable peptide sequence among the total number of amino acid residues that constitute the peptide chain) provided radiosensitizing activity that increases radiosensitivity of target tumor cells is not lost, the ratio is preferably roughly 60% or more, more preferably 80% or more and particularly preferably 90% or more. A peptide constituted of a radiosensitizing peptide sequence and membrane-permeable peptide sequence (namely, a peptide in which these sequences account for 100% of the entire amino acid sequence) is a preferable form thereof.

Furthermore, although that in which all amino acid residues are L-amino acids is preferable for the radiosensitizing synthetic peptide of the present invention, all or a portion of the amino acid residues may be replaced with D-amino acids provided radiosensitizing activity that increases radiosensitivity of tumor cells is not lost.

The radiosensitizing synthetic peptide disclosed herein can be easily produced in compliance with ordinary chemical synthesis methods. For example, a conventionally known solid-phase synthesis method or liquid-phase synthesize method may be employed. A solid-phase synthesis method using a Boc (t-butyloxycarbonyl) group or Fmoc (9-fluorenylmethyloxycarbonyl) group as an amino group protecting group is preferable.

The peptide chain of the radiosensitizing synthetic peptide disclosed herein having a desired amino acid sequence and modified moiety (such as C-terminal amidation) can be synthesized by a solid-phase synthesis method using a commercially available peptide synthesizer (such as that available from Intavis AG or Protein Technologies, Inc.).

Alternatively, a radiosensitizing synthetic peptide may be biosynthesized based on a genetic engineering technique. Namely, a polynucleotide (typically DNA) is synthesized that has a nucleotide sequence (containing an ATG start codon) encoding the amino acid sequence of a desired radiosensitizing synthetic peptide. A recombinant vector, having an expression gene construct constituted of the synthesized polynucleotide (DNA) and various regulatory elements for expressing the amino acid sequence thereof in host cells (including a promoter, ribosome binding site, terminator, enhancer and various cis elements for controlling expression level), is then constructed corresponding to the host cells.

According to a common technique, this recombinant vector is introduced into prescribed host cells (such as yeast, insect cells or plant cells), and the host cells or tissues or individuals containing the host cells are cultured under prescribed conditions. As a result, a target peptide can be expressed and produced in the cells. By then isolating the peptide from the host cells (from a medium in the case of being secreted) and carrying out folding or purification and the like as necessary, a target radiosensitizing synthetic peptide can be obtained.

Furthermore, methods conventionally carried out in the relevant fields may be used without modification for the methods used to construct the recombinant vector and introduce the constructed recombinant vector into host cells, and since the methods per se do not particularly characterize the present invention, detailed explanations thereof are omitted.

For example, a fused protein expression system can be used to produce peptides in host cells both efficiently and in large volume. Namely, a gene (DNA) encoding the amino acid sequence of a target radiosensitizing synthetic peptide is synthesized chemically, and the synthesized gene is introduced into a preferable site of a suitable fused protein expression vector (such as a glutathione S-transferase (GST) fused protein expression vector in the manner of a member of the pET Series available from Novagen Inc. or a member of the pGEX Series available form Amersham Biosciences Ltd.). Host cells (typically, *Escherichia coli* cells) are then transformed by the vector. The resulting transformant is cultured to prepare the target fused protein. Next, the protein is extracted and purified. Next, the resulting purified fused protein is cleaved with a prescribed enzyme (protease), and the free target fragment (designed radiosensitizing synthetic peptide) is recovered by a method such as affinity column chromatography. In addition, refolding is carried out as necessary using a suitable method. The use of such a conventionally known fused protein expression system (such as the GST/His System available from Amersham Biosciences Ltd.) makes it possible to produce the radiosensitizing synthetic peptide disclosed herein.

Alternatively, a target polypeptide can be synthesized in vitro by employing a so-called cell-free protein synthesis system by constructing template DNA for a cell-free protein synthesis system (namely, a synthetic gene fragment containing a nucleotide sequence encoding the amino acid sequence of a radiosensitizing synthetic peptide) and using various compounds required for peptide synthesis (such as ATP, RNA polymerase and amino acids). The paper by Shimizu et al. (Shimizu et al., Nature Biotechnology, 19, 751-755 (2001)) and the paper by Madin et al. (Madin et al., Proc. Natl. Acad. Sci. USA, 97(2), 559-564 (2000)), for example, can be referred to regarding cell-free protein synthesis systems. Numerous corporations were already engaged in commission product of polypeptides as of the filing date of the present application based on the technologies descried in this literature, and cell-free protein synthesis kits (such as the PROTEIOS™ wheat germ cell-free protein synthesis kit available from Japan's CellFree Sciences Co., Ltd.) were commercially available.

A single-stranded or double-stranded polynucleotide containing a nucleotide sequence encoding the radiosensitizing synthetic peptide disclosed herein and/or a nucleotide sequence complementary to that sequence can be easily produced (synthesized) according to conventionally known methods. Namely, a nucleotide sequence corresponding to the amino acid sequence of a radiosensitizing synthetic peptide is easily determined and provided by selecting codons corresponding to each amino acid residue that constitutes a designed amino acid sequence. Once the nucleotide sequence is determined, a polynucleotide (single strand) corresponding to a desired nucleotide sequence can be easily obtained by using a DNA synthesizer and the like. Moreover, target double-stranded DNA can be obtained by employing various types of enzymatic synthesis means (and typically, PCR) by using the resulting single-stranded DNA as a template. In addition, the polynucleotide may be in the form of DNA or RNA (mRNA). DNA can be provided in the form of a double strand or single strand. In the case of providing in the form of a single strand, it may be a coding strand (sense strand) or non-coding strand (antisense strand) of a sequence complementary thereto.

A polynucleotide obtained in this manner can be used as a material for constructing a recombinant gene (expression cassette) for producing a radiosensitizing synthetic peptide in various types of host cells or using a cell-free protein synthesis system as previously described.

The radiosensitizing synthetic peptide disclosed herein is able to increase the sensitivity to radiation in at least one type of tumor cell by acting on that tumor cell. Consequently, it can be preferably used as the active ingredient of a composition used to increase the radiosensitivity of tumor cells (radiosensitizing composition). Furthermore, the radiosensitizing synthetic peptide disclosed herein may also be in the form of a salt provided it does not impair the radiosensitizing activity thereof. For example, an acid addition salt of the peptide can be used that can be obtained by subjecting an ordinarily used inorganic acid or organic acid to an addition reaction in accordance with ordinary methods. Alternatively, the peptide may be in the form of other salts (such as metal salts) provided the peptide retains the radiosensitizing activity thereof. Thus, a "peptide" as described in the present specification and claims includes that in the form of a salt.

The radiosensitizing composition provided by the present invention is a composition used to increase the radiosensitivity of at least one type of tumor cell (and typically, a pharmacological composition such as a pharmaceutical composition), and is characterized by containing at least one type of the radiosensitizing synthetic peptide disclosed herein as an active ingredient thereof (namely, a substance involved in increasing the radiosensitivity of target tumor cells). This radiosensitizing composition can be preferably used as a pharmaceutical composition used to increase the radiosensitivity of tumor cells in tumor radiation therapy (so-called radiosensitizer), or in other words, as an assistant in tumor radiation therapy.

Furthermore, there are no particular limitations on methods used to prepare, storage or use components and drugs other than the radiosensitizing synthetic peptide able to be contained in the radiosensitizing composition, and for example, and may be the same as conventional peptide preparations (pharmacological compositions containing peptides as active ingredients thereof).

The radiosensitizing composition disclosed herein can contain various types of pharmacologically (pharmaceutically) acceptable vehicles corresponding to the form of use thereof provided the active ingredient thereof in the form of the radiosensitizing synthetic peptide can be stored in a state in which the radiosensitizing activity thereof is not lost. Vehicles commonly used as diluents or excipients and the like in peptide pharmaceuticals are preferable. Although suitably varying according to the application or form of the radiosensitizing composition, typical examples include water, physiological buffers and various types of organic solvents. The vehicle can be an aqueous alcohol (such as ethanol) solution having a suitable concentration, glycerol or non-drying oil in the manner of olive oil. Alternatively, the vehicle may be a liposome. In addition, examples of secondary components able to be contained in the radiosensitizing composition include various types of fillers, thickeners, binders, humidifying agents, surfactants, pigments and fragrances.

There are no particular limitations on the form of the radiosensitizing composition. Examples of typical forms include a liquid, suspension, emulsion, aerosol, foam, granules, powder, tablets, capsules, ointment and aqueous gel. In addition, it can also be in the form of freeze-dried preparation or granules used to prepare a drug solution by dissolving in physiological saline or buffer (such as PBS) immediately prior to use.

Furthermore, the process per se used to prepare various forms of drugs (compositions) by using the radiosensitizing synthetic peptide (active ingredient) and various vehicles (auxiliary components) as materials may be in compliance with a conventionally known method, and since the preparation method per se does not characterize the present invention, a detailed explanation thereof is omitted. An example of an information source relating to formulation is Comprehensive Medical Chemistry, Corwin Hansch, ed., Pergamon Press (1990). The entire contents of this publication are incorporated in the present specification by reference.

There are no particular limitations on the applicable target cells of the radiosensitizing composition disclosed herein (or the radiosensitizing synthetic peptide contained in the composition), and the radiosensitivity of various tumor cells can be increased. Human cells or cells of animals other than humans (such as vertebrates and particularly mammals) are particularly preferable as application targets. Human cells are preferable from the viewpoint of medical utility value, and tumor cells constituting malignant tumors (so-called cancer cells) are preferable as application targets. Examples of malignant tumors (namely, application target cells) used as application targets of the radiosensitizing composition disclosed herein (or radiosensitizing synthetic peptide contained in the composition) include prostate cancer, cervical cancer, breast cancer, gallbladder cancer, pancreatic cancer, colon cancer, rectal cancer, kidney cancer, lung cancer, esophageal cancer, laryngeal cancer, pharyngeal cancer, thyroid cancer, thymic carcinoma, ovarian cancer, salivary gland cancer, stomach cancer, basal cell carcinoma, leukemia, malignant lymphoma, multiple myeloma, medulloblastoma, retinoblastoma, neuroblastoma, malignant glioma, melanoma (malignant melanoma), mesothelioma and sarcoma. For example, tumor cells derived from epithelial malignant tumors, and typically tumor cells constituting squamous cell carcinoma or tumor cells constituting adenoma, are preferable as application targets. Since adenoma generally tends to have lower radiosensitivity than squamous cell carcinoma, there is considerable benefit in applying the radiosensitizing composition disclosed herein (or the radiosensitizing synthetic peptide contained in the composition) to increase the radiosensitivity of tumor cells constituting adenoma.

Furthermore, radiosensitivity varies according to the type of tumor (typically, a malignant tumor, namely cancer). The radiosensitizing composition (or radiosensitizing synthetic peptide contained in the composition) can be applied without any particular limitations on a tumor (cancer) capable of undergoing ordinary radiation therapy, or in other words, a tumor having comparatively high radiosensitivity (namely, tumor cells constituting the tumor). On the other hand, even in the case of a tumor (cancer) having low radiosensitivity, by applying the radiosensitizing composition (or radiosensitizing synthetic peptide) disclosed herein and increasing the radiosensitivity of tumor cells constituting that tumor, the therapeutic effect of radiation therapy performed on this tumor (cancer) having low radiosensitivity can be expected to be improved. Examples of such tumors (cancer) having comparatively low sensitivity to radiation include prostate cancer, cervical cancer, breast cancer, gallbladder cancer, pancreatic cancer, colon cancer, rectal cancer, kidney cancer, lung cancer, esophageal cancer, pharyngeal cancer, stomach cancer, melanoma (malignant melanoma), mesothelioma and sarcoma.

In addition, tumor cells having a low intracellular oxygen concentration (to also be referred to as "hypoxic tumor cells") tend to have lower radiosensitivity in comparison with tumor cells having a high intracellular oxygen concentration. Thus, the radiosensitizing composition (or radiosensitizing synthetic peptide) disclosed herein can be effectively applied to hypoxic tumor cells. Furthermore, tumor cells present in the marginal portion of a solid tumor tend to have a sufficiently high intracellular oxygen concentration, while tumor cells in the central portion of a solid tumor tend to have a low intracellular oxygen concentration. Consequently, in other words, the radiosensitizing composition disclosed herein (or the radiosensitizing synthetic peptide contained in the composition) can be preferably applied to tumor cells present in the central portion of a solid tumor.

Furthermore, a solid tumor is a tumor that proliferates in the form of a mass of cells in a specific organ, tissue or gland, and since it is easy to limit the irradiated range, it is a typical tumor in which the therapeutic effect of radiation therapy can be expected to be demonstrated. Consequently, the radiosensitizing composition disclosed herein (or the radiosensitizing synthetic peptide contained in the composition) can be preferably applied to a solid tumor (namely, tumor cells derived from the solid tumor).

The radiosensitizing composition (or radiosensitizing synthetic peptide) disclosed herein can be used by a method or at a dosage that corresponds to the form and objective thereof.

For example, in the case of increasing the radiosensitivity of target cells (namely, tumor cells constituting a tumor targeted for treatment) in vivo, a suitable amount of the radiosensitizing composition disclosed herein (namely, the active ingredient of the composition in the form of a radiosensitizing synthetic peptide) can be administered in a desired amount to patient (namely, in vivo) by injecting in the form of a liquid preparation intravenously, intramuscularly, subcutaneously, intracutaneously or into the nasal cavity or peritoneal cavity and the like. Alternatively, a solid preparation such as tablets, a gel-like preparation such as an ointment, or an aqueous jelly can be administered directly into the target tissue (such as an affected area such as a tissue or organ containing tumor cells) or in the proximity of that tissue. Alternatively, a solid preparation can be administered orally or in the form of a suppository, enema or inhalation. In the case of oral administration, an encapsulated form or protective (coating) material is preferably applied to inhibit decomposition by digestive enzymes in the digestive tract. Furthermore, the dosage of the radiosensitizing composition disclosed herein given to a patient, the administration frequency thereof and the administration form thereof are design matters that can be suitably varied according to such factors as the status (symptoms), age, body weight and gender of the patient to be treated, type, form, location and staging of the administration target (tumor), as well as form of the radiosensitizing composition used, concentration of radiosensitizing synthetic peptide contained in the radiosensitizing composition, and presence or absence and concentrations of auxiliary components other than the synthetic peptide. A person with ordinary skill in the art would be able to prepare or formulate a radiosensitizing composition of a suitable form based on the known art in the form of pharmacological, clinical, physiological and hygienic findings, in addition to engineering findings relating to peptide preparations, depending on the circumstances. For example, in the case of administration by injection, the dosage per day can be about 1 µg/kg to 100 mg/kg (and preferably 10 µg/kg to 10 mg/kg) as the amount of peptide contained in radiosensitizing composition.

Alternatively, in the case of increasing the radiosensitivity of tumor cells cultured (sub-cultured) outside the body (in vitro) (including the case of a cell mass, tissue or organ excised from the body), a suitable amount of the radiosensitizing composition (radiosensitizing synthetic peptide) disclosed herein is supplied at least once to target cultured cells (cell culture) at any stage during the course of culturing (and preferably after having cultured (proliferated) or sub-cultured for a prescribed period of time) in a medium. Examples of the cultured cells include established cell lines and primary cultured cells or cellular materials temporarily or permanently removed from the body (such as cells or viable tissue cells).

There are no particular limitations on the supplied amount of the radiosensitizing composition (radiosensitizing synthetic peptide) per round of culturing or the number of times supplied since it can vary according to conditions such as the type of cultured cells, cell density (cell density at the start of culturing), number of transfers, culturing conditions or type of medium. For example, in the case of culturing cells derived from a human or non-human animal (typically, a vertebrate, and particularly a mammal), the radiosensitizing composition (radiosensitizing synthetic peptide) is preferably supplied once to a plurality of times to the cultured cells (cell culture) so that the peptide concentration in the medium is about 0.1 µM to 100 µM and preferably 0.5 µM to 80 µM (for example, 1 µM to 50 µM) (by, for example, supplying at the start of culturing and additionally supplying during cell transfer and when replacing the medium).

In addition, the radiosensitizing composition disclosed herein (or the radiosensitizing synthetic peptide contained in the composition) can also be used in combination with other substances that demonstrate antitumor effects corresponding to, for example, the objective and type of target cells. Examples of other substances demonstrating antitumor effects include anticancer agents such as alkylating agents, metabolic antagonists, microtubule agents, platinum preparations, antitumor antibiotics, hormone drugs or molecular target drugs, and radioprotective agents used to prevent the proliferation of normal cells from being inhibited by radiation therapy (used to lower the radiosensitivity of normal cells).

As will be made clear from the examples to be subsequently described, the radiosensitizing composition disclosed herein (or the radiosensitizing synthetic peptide contained in the composition) is able to effectively inhibit the proliferation of tumor cells by irradiating with radiation after having supplied the synthetic peptide (or the composition) to the tumor cells.

Thus, according to the present invention, a method for inhibiting the proliferation of tumor cells can be provided that is characterized by supplying the radiosensitizing composition disclosed herein (or the radiosensitizing synthetic peptide contained in the composition) to at least one type of target tumor cell either in vivo or in vitro (such as by adding to a culture broth used to culture tumor cells) and subsequently irradiating the tumor cells with radiation.

In addition, according to the present invention, a method for treating a tumor can be provided that is characterized by administering at least one type of the radiosensitizing synthetic peptide disclosed herein (namely, a pharmaceutical composition containing that peptide) to a patient and subsequently irradiating the affected area (namely, the patient) with radiation.

In the method for inhibiting the proliferation of tumor cells and method for treating a tumor disclosed herein, radiation commonly used in tumor radiation therapy can be used without any particular limitations. For example, any of X-rays or electromagnetic waves having a wavelength shorter than that of X-rays, a proton beam or a heavy particle beam using ions having a mass equal to or greater than helium (such as a carbon ion beam) can be used. High-energy X-rays of 4 MV (megavolts) to 20 MV (and typically, 4 MV, 6 MV or 10 MV) can be used for the X-rays. In addition, examples of electromagnetic waves having a wavelength shorter than that of X-rays include γ rays emitted from radioactive substances such as cobalt 60 ($^{60}$Co), iodine 125 ($^{125}$I), iridium 192 ($^{192}$Ir), cesium 137 ($^{137}$Cs) or gold 198 ($^{198}$Au), and β rays emitted from radioactive substances such as iodine 131 ($^{131}$I), strontium 89 ($^{89}$Sr) or yttrium 90 ($^{90}$Y). X-rays are used preferably from the viewpoint of the popularity of radiation devices using X-rays. On the other hand, heavy particle beams enable tumors to be irradiated locally (at the affected area of a tumor) at a high dose and enable effective treatment to be realized while reducing damage to normal cells caused by irradiation. From this viewpoint, heavy particle beams (and typically, a carbon ion beam) can be used preferably.

In the method for inhibiting proliferation of tumor cells disclosed herein, the method used to irradiate with radiation can be suitably set corresponding to the type of radiation and target tumor cells.

For example, in the case of inhibiting the proliferation of tumor cells cultured (sub-cultured) outside the body (in vitro) (including the case of a cell mass, tissue or organ excised from the body), tumor cells in a culture vessel may be irradiated a suitable number of times with a suitable dose of radiation. For example, in the case of irradiating tumor cells with X-rays, the target tumor cells are preferably irradiated one to a plurality of times with radiation so that the total dose is 5 gray (5 Gy) or less, and for example, 3 gray (3 Gy) or less.

Alternatively, in the case of inhibiting the proliferation of tumor cells present in the body, target tumor cells are irradiated a suitable number of times with a suitable dose of radiation from outside the body. This radiation from outside the body is typically radiated locally at the portion where the tumor cells are present (namely, the location where the tumor is present). Alternatively, by introducing a medical material that emits radiation (typically containing a radioisotope) into the body (such as by inserting or attaching to tumor tissue or implanting within a lumen), or administering a radioactive substance having affinity for the tumor cells into the body (by, for example, injection or oral administration), the target tumor cells may be irradiated from inside the body (so-called implant irradiation).

Furthermore, in the cell proliferation inhibition method disclosed herein, the dose of radiation irradiated onto target tumor cells and the frequency of that irradiation and the like are design matters that can be suitably varied according to such factors as the status (symptoms), age, body weight and gender of the patient to be treated, type, form, location and staging of the administration target (tumor), as well as the type of radiation used, irradiation method and equipment used to radiate radiation. A person with ordinary skill in the art would be able to suitably set a suitable dose and irradiation frequency of radiation used to irradiate tumor cells based on the known ark in the form of pharmacological, clinical, physiological and hygienic findings, in addition to findings relating to tumor radiation therapy. For example, in the case of irradiating with X-rays, X-rays can be radiated so that the total dose is 100 Gy or less (preferably 80 Gy or less, more preferably 50 Gy or less and even more preferably 30 Gy or less). X-rays may be radiated at a frequency of 20 to 50 times (preferably 25 to 40 times) every 1 to 2 days.

In the method for inhibiting the proliferation of tumor cells disclosed herein, in the case of irradiating tumor cells with radiation a plurality of times, it is preferable to supply the radiosensitizing synthetic peptide (namely, the radiosensitizing composition containing the peptide) to the tumor cells a plurality of times prior to irradiation.

In addition, there are no particular limitations on the amount of time until the target tumor cells are irradiated after supplying the radiosensitizing synthetic peptide (namely, the radiosensitizing composition containing the peptide) to the target tumor cells (typically by adding to the medium used to culture the tumor cells or administering to a patient). For example, it is preferable to provide an amount of time sufficient for increasing radiosensitivity of the target tumor cells. Typically, the target tumor cells are preferably irradiated several hours (typically, 6 hours or more, and for example, 12 hours or more) or within several days (typically, within 3 days, and for example, within 2 days) after having supplied the radiosensitizing synthetic peptide (namely, the radiosensitizing composition containing the peptide) to the target tumor cells.

In addition, in the tumor treatment method disclosed herein, there are no particular limitations on the method used to irradiate the tumor cells. For example, the tumor cells may be irradiated locally at a suitable dose at a portion where the tumor (typically, a malignant tumor or cancer) is present from outside the body of a patient. In the tumor treatment method disclosed herein, the tumor cells are typically irradiated consecutively for a plurality of times every day or every few days. At this time, the radiosensitizing synthetic peptide (namely, a pharmaceutical composition containing the peptide) is also consecutively administered to a patient prior to irradiation.

Alternatively, similar to the case of the method for inhibiting proliferation of tumor cells, by introducing a medical material that emits radiation (typically containing a radioisotope) into the body (such as by inserting or attaching to tumor tissue or implanting within a lumen), or administering a radioactive substance having affinity for the tumor cells into the body (by, for example, injection or oral administration), the target tumor may be irradiated from inside the body (so-called implant irradiation).

Furthermore, in the tumor treatment method disclosed herein, the dose of irradiated radiation and the frequency of that irradiation and the like are design matters that can be suitably varied according to such factors as the status (symptoms), age, body weight and gender of the patient to be treated, type, form, location and staging of the administration target (malignant tumor), as well as the type of radiation used, irradiation method and equipment used to radiate radiation. A person with ordinary skill in the art would be able to suitably set a suitable dose and irradiation frequency of the radiation based on the known art in the form of pharmacological, clinical, physiological and hygienic findings, in addition to findings relating to tumor radiation therapy. For example, in the case of irradiating with X-rays, X-rays can be radiated onto the affected area of the tumor (namely, a patient) so that the total dose is 100 Gy or less (preferably 80 Gy or less, more preferably 50 Gy or less and even more preferably 30 Gy or less). For example, X-rays may be radiated at a frequency of 20 to 50 times (preferably 25 to 40 times) every 1 to 2 days.

Furthermore, in the tumor treatment method disclosed herein, there are no particular limitations on the amount of time until a portion where a tumor (typically, a malignant tumor or cancer) is present is irradiated after administering the radiosensitizing synthetic peptide (namely, a pharmaceutical composition containing the peptide) to a patient. For example, it is preferable to provide an amount of time sufficient for increasing radiosensitivity of the tumor cells that constitute the tumor. Typically, the tumor is preferably irradiated several hours (typically, 6 hours or more, and for example, 12 hours or more) or within several days (typically, within 3 days, and for example, within 2 days) after having administered the radiosensitizing synthetic peptide (namely, a pharmaceutical composition containing the peptide) to the patient.

Although the following provides an explanation of several examples relating to the present invention, it is not intended to limit the present invention to that indicated in the examples.

Example 1: Peptide Synthesis

A radiosensitizing synthetic peptide in the form of a peptide constituted of the radiosensitizing peptide sequence of CKSKSRRSC (SEQ ID NO. 1) was synthesized by solid-phase synthesis (Fmoc method) according to the manual using a commercially available peptide synthesizer (Intavis AG). A linear synthetic peptide constituted of a total of nine amino acid residues was named "Sample 1". Furthermore, since the manner of use per se of the peptide synthesizer does not characterize the present invention, a detailed explanation thereof is omitted. The synthesized Sample 1 was dissolved in PBS(−) to prepare a peptide stock solution.

Example 2: Evaluation Test of Radiosensitizing Activity of Synthetic Peptide

Radiosensitizing activity of the radiosensitizing synthetic peptide (Sample 1) obtained in Example 1 was evaluated by measuring cell survival rates during culturing after having irradiated test cells supplied with the radiosensitizing synthetic peptide with radiation (here, X-rays).

Figure 1:
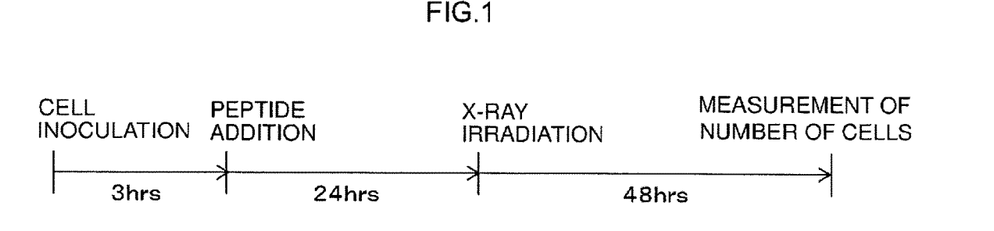
FIG. 1 is a drawing (time chart) schematically indicating cell culturing conditions in an example.

Human carcinoma-derived cells (HeLaS3 cells) and cells derived from normal human tissue (CCD-1079Sk cells) were used for the test cells. As shown in Table 1, each of the test cells were cultured while changing the peptide concentration in the medium and the radiation dose followed by measurement of cell survival rates. Furthermore, a time chart of cell culturing in this evaluation test is shown in FIG. 1. Details of the evaluation test are as indicated below.

TABLE 1

| Test Group | Test Cells | Peptide Concentration | X-ray Dose |
|---|---|---|---|
| 1 | HeLaS3 | 50 μM | 0 Gy |
| 2 | | 0 μM | |
| 3 | | 50 μM | 2 Gy |
| 4 | | 0 μM | |
| 5 | CCD-1079Sk | 50 μM | 0 Gy |
| 6 | | 0 μM | |
| 7 | | 50 μM | 3 Gy |
| 8 | | 0 μM | |

First, a cultured cell line derived from human cervical cancer in the form of HeLaS3 cells (ATCC™ CCL2.2) were prepared for use as test cells derived from a human tumor. In addition, a cultured fibroblast cell line derived from human skin tissue in the form CCD-1079Sk cells (ATCC™ CRL-2097) was prepared for use as test cells derived from normal human tissue.

Each of the test cells were inoculated into a 48-well plate to the prescribed number of cells followed by pre-culturing for about 3 hours in an incubator under conditions of 5% $CO_2$ and 37° C. until the cells adhered to the bottom of the culture vessel. Furthermore, the amount of medium per well was 200 μL for each of the test cells.

The HeLaS3 cells were inoculated into each well of a 48-well plate so that the number of cells per well was roughly $1 \times 10^4$ cells. Ordinary Dulbecco's modified eagle's medium (DMEM), namely DMEM (Wako Pure Chemical Industries, Ltd., Cat. No. 043-30085) containing 10% FBS, 50 units/mL of penicillin and 50 μg/mL of streptomycin, was used for the medium.

The CCD-1079Sk cells were inoculated into each well of a 48-well plate so that the number of cells per well was roughly $1 \times 10^4$ cells. Ordinary Dulbecco's modified eagle's medium (DMEM), namely DMEM (Wako Pure Chemical Industries, Ltd., Cat. No. 043-30085) containing 10% FBS, 50 units/mL of penicillin and 50 μg/mL of streptomycin, was used for the medium.

Following completion of pre-culturing for the prescribed amount of time, the medium in the culture vessel was replaced with medium obtained by further adding Sample 1 to DMEM medium containing 10% FBS (but not containing penicillin or streptomycin) in an amount so that the peptide concentration was 50 μM (Test Groups 1, 3 5 and 7). Furthermore, a peptide non-addition groups were provided for comparison in which only PBS(−) was added in an amount equal to the amount peptide stock solution added to the peptide addition groups (Test Groups 2, 4, 6 and 8).

Following addition of the sample peptides (or PBS(−)) as described above, the 48-well plates were arranged in a $CO_2$ incubator and cultured for 24 hours under conditions of 37° C. and 5% $CO_2$.

Next, after culturing for a prescribed amount of time (24 hours) in the presence of the peptide, each of the test cells in the culture vessels were irradiated with X-rays (Test Groups 3, 4, 7 and 8). Here, each of the test cells were irradiated with X-rays at a dose rate of 0.24 gray/second (0.24 Gy/sec). Furthermore, the doses at which each of the test cells were irradiated were 2 gray (2 Gy) for the HeLaS3 cells and 3 gray (3 Gy) for the CCD-1079Sk cells. In addition, test groups not irradiated with X-rays (namely, dose=0 Gy) were provided for comparison (Test Groups 1, 2, 5 and 6).

Following completion of X-ray irradiation as described above, the 48-well plates were arranged in a $CO_2$ incubator and cultured for 48 hours under conditions of 37° C. and 5% $CO_2$.

Next, at the point 48 hours had elapsed following X-ray irradiation, the viability of the test cells (the number of viable cells) was measured using a commercially available chromogenic assay kit (Cell Counting Kit-8, Dojindo Molecular Technologies, Inc.). Namely, the number of viable cells was measured by colorimetry by quantifying the amount of water-soluble formazan in the medium by measuring using absorption spectrophotometry (measuring wavelength: 450 nm, reference wavelength: 650 nm) based on the principle that the tetrazolium salt in the reagent is reduced by enzyme activity of viable cells resulting in the formation of water-soluble formazan. Furthermore, the procedure was carried out in accordance with the manual provided with the assay kit with the exception of the procedures described in detail below.

More specifically, after the prescribed culturing time had elapsed, 20 μL aliquots of a reagent containing a chromogenic substrate in the form of "Water-Soluble Tetrazolium Salt (WST-8)" were added to each of the wells of the cell culture plates followed by incubating for 1 hour under conditions of 5% $CO_2$ and 37° C. In addition, 20 μL of the chromogenic substrate (WST-8) were added to 200 μL of the medium (DMEM medium) used to culture each of the test cells followed by incubating for 1 hour under conditions of 5% $CO_2$ and 37° C. to serve as a colorimetry blank. Subsequently, 100 μL aliquots of the cell culture broth in each well to which the chromogenic reagent had been added were dispensed into each well of a 96-well plate. Next, optical absorbance at a wavelength of 450 nm ($A_{450}$) and optical absorbance at 650 nm ($A_{650}$) were measured for the cell culture broth dispensed into the 96-well plate using a spectrophotometer (microplate reader). The values of $A_{450-650}$, obtained by correcting the $A_{450}$ value of each test group for reference wavelength absorbance ($A_{650}$) and the blank value, were calculated using the equation: $A_{450-650}$= ($A_{450}$–$A_{650}$ of each test group)–($A_{450}$–$A_{650}$ of blank).

The cell survival rate (%) of each test group based on a value of 100% for the cell survival rate in test group to which peptide was not added and was not irradiated with X-rays (control group) was calculated for each of the test cells was calculated according to the equation: cell survival rate (%)=($A_{450-650}$ of each test group)/($A_{450-650}$ of control group)×100.

Namely, cell survival rates (%) of each test group based on a value of 100% for the cell survival rate in Test Group 2 were determined for Test Groups 1-4 using HeLaS3 cells for the test cells. The results are shown in FIG. 2.

Figure 3:
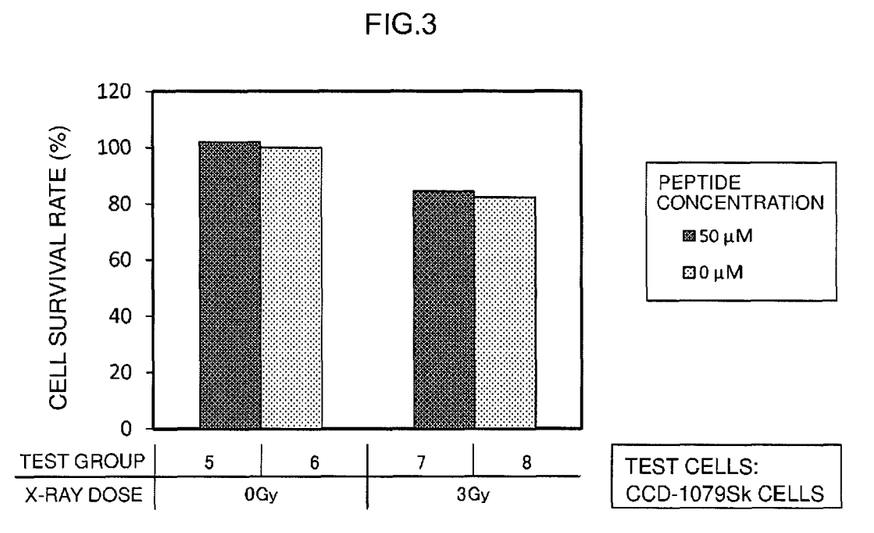
FIG. 3 is graph indicating the results for cell survival rates of CCD-1079Sk cells cultured for a prescribed amount of time in a medium containing a radiosensitizing synthetic peptide according to an example (Sample 1) and then irradiated with X-rays. The number of each test group is plotted on the horizontal axis of the graph. The cell survival rates of each test group are plotted on the vertical axis as a ratio (%) based on a value of 100% for the cell survival rate of a test group 6 to which peptide has not been added and which has not been irradiated with X-rays.

In addition, cell survival rates (%) of each test group based on a value of 100% for the cell survival rate in Test Group 6 were determined for Test Groups 5-8 using CCD-1079Sk cells for the test cells. Those results are shown in FIG. 3.

Figure 2:
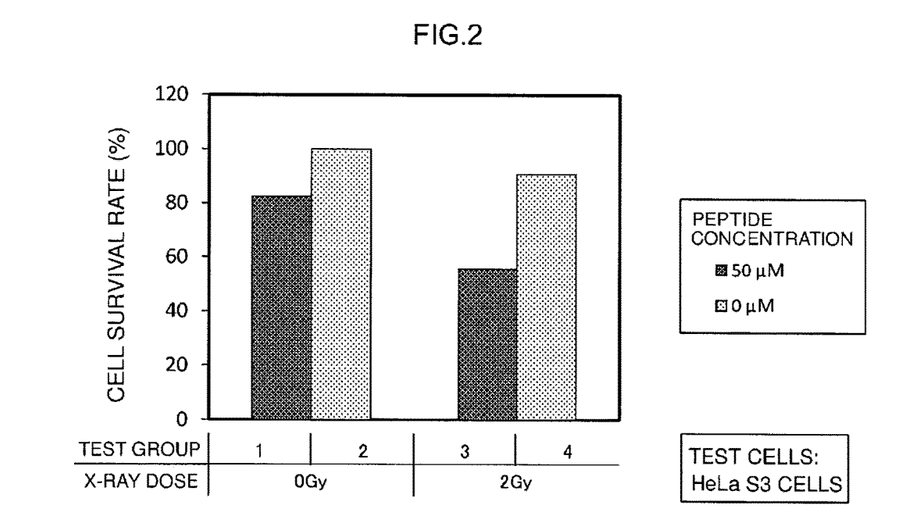
FIG. 2 is graph indicating the results for cell survival rates of HeLa S3 cells cultured for a prescribed amount of time in a medium containing a radiosensitizing synthetic peptide according to an example (Sample 1) and then irradiated with X-rays. The number of each test group is plotted on the horizontal axis of the graph. The cell survival rates of each test group are plotted on the vertical axis as a ratio (%) based on a value of 100% for the cell survival rate of a test group 2 to which peptide has not been added and which has not been irradiated with X-rays.

As shown in FIG. 2, with respect to HeLaS3 cells derived from human carcinoma, Test Group 3, in which the cells were cultured after adding peptide according to Sample 1 to a culture broth of the cells followed by irradiating with X-rays, demonstrated a remarkable lower cell survival rate in comparison with Test Group 4, in which peptide was not added but was irradiated with X-rays. Namely, proliferation of tumor cells in Test Group 3 was remarkably inhibited.

In contrast, the cell survival rate in Test Group 4 was nearly equal to the cell survival rate of Test Group 2. Namely, there was hardly any change in cell survival rate in the case of only irradiating the HeLaS3 cells with X-rays at 2 Gy.

Furthermore, cell survivability in Test Group 1 was slightly lower in comparison with Test Group 2. This is thought to be due to the effect of cytotoxicity (inhibition of cell proliferation) attributable to the peptide according to Sample 1. However, the degree of the decrease in cell survival rate in Test Group 3 relative to Test Group 4 was remarkable in comparison with the degree of the decrease in cell survival rate in Test Group 1 relative to Test Group 2.

These results indicate that the peptide according to Sample 1 increased the radiosensitivity of the HeLaS3 cells to X-rays. In other words, the proliferation of target tumor cells was confirmed to be able to be remarkably inhibited by supplying the peptide according to Sample 1 to the target tumor cells (here, HeLaS3 cells) followed by irradiating the cells with X-rays.

On the other hand, as shown in FIG. 3, in the case of CCD-1079Sk cells derived from normal human tissue, the cell survival rate in Test Group 7, in which the cells were cultured by adding the peptide according to Sample 1 to a culture broth of the cells followed by irradiating with X-rays, was nearly the same as the cell survival rate in comparison with Test Group 8 to which peptide was not added. In addition, the degree of the decrease in the cell survival rate of Test Group 7 relative to Test Group 5 was nearly the same as the degree of decrease in cell survival rate of Test Group 8 relative to Test Group 6. Namely, there was no change in X-ray sensitivity in CCD-1079Sk cells even if the peptide according to Sample 1 was added.

Furthermore, the degree of the decrease in cell survival rate of Test Group 8 relative to Test Group 6 was slightly larger than the degree of the decrease in cell survival rate of Test Group 4 relative to Test Group 2. This is thought to be due to the X-ray dose used to irradiate CCD-1079Sk cells being higher than the X-ray dose used to irradiate HeLaS3 cells.

The above results indicate that the synthetic peptide used as sample is a radiosensitizing synthetic peptide having the ability to be able to increase the radiosensitivity of tumor cells as a result of being supplied to those tumor cells, and indicate that the activity of this synthetic peptide that causes an increase in radiosensitivity is demonstrated specifically in tumor cells. Namely, the above results indicate that the synthetic peptide used as sample is useful as an active ingredient of a composition for specifically increasing the radiosensitivity of tumor cells (namely, a radiosensitizing composition). In addition, the above results also indicate that supplying the synthetic peptide used as sample to target tumor cells followed by irradiating with X-rays makes it possible to inhibit proliferation of the target tumor cells.

Namely, the above results indicate that the radiosensitizing synthetic peptide disclosed herein (namely, the radiosensitizing composition containing that peptide) has activity that increases the radiosensitivity of tumor cells, and indicates that the use of the radiosensitizing synthetic peptide (namely, the radiosensitizing composition containing that peptide) makes it possible to effectively inhibit the proliferation of tumor cells.

Example 3: Evaluation Test of Radiosensitizing Activity of Synthetic Peptide on Tumor Tissue Furthermore, although the detailed test procedure and results are not indicated here, the radiosensitizing activity of the radiosensitizing synthetic peptide (Sample 1) obtained in Example 1 was evaluated by targeting tumor tissue removed from the body. As a result, tumor tissue that supplied with the peptide, irradiated with X-rays and then cultured for a prescribed amount of time exhibited a remarkable decrease in tumor tissue volume in comparison with tumor tissue to which the peptide was not added or not irradiated with X-rays. Namely, administration of radiosensitizing synthetic peptide disclosed herein (namely, a pharmaceutical composition containing the peptide) to a patient followed by irradiating the tumor tissue with X-rays was confirmed to be able to realize effective tumor treatment.

Example 4: Preparation of Granules

After mixing 50 mg of the synthetic peptide according to Sample 1 (radiosensitizing synthetic peptide) with 50 mg of crystalline cellulose and 400 mg of lactose, 1 mL of a mixture of ethanol and water was added and kneaded. This kneaded product was then granulated in accordance with ordinary methods to obtain granules having as the main component thereof the radiosensitizing synthetic peptide disclosed herein (granular composition).

As has been described above, since the radiosensitizing synthetic peptide disclosed herein has activity that specifically increases the radiosensitivity of tumor cells, it can be preferably used for the purpose of increasing the radiosensitivity of target tumor cells. Thus, a composition containing the radiosensitizing synthetic peptide disclosed herein can be preferably used as a pharmaceutical composition (typically, a radiosensitizing composition) for increasing the radiosensitivity of target tumor cells in tumor radiation therapy. The use of this composition makes it possible to provide a method for inhibiting the proliferation of tumor cells and a tumor treatment method.

[Sequence Listings Free Text]

SEQ ID NOS. 1-8 Synthetic Peptides

What is claimed is:

1. A pharmaceutical composition for use in increasing a sensitivity of tumor cells to radiation in tumor radiation therapy, the composition comprising:
   a pharmaceutically acceptable vehicle; and
   a synthetic peptide having a radiosensitizing peptide sequence including a following amino acid sequence $CX_2X_3KX_5X_6X_7X_8C$ wherein
   $X_2$ represents K or R,
   $X_3$ represents S or A,
   $X_5$ represents S or A,
   $X_6$ represents R or G,
   $X_7$ represents R or D and
   $X_8$ represents S or P, with the proviso that when $X_2$ is R, $X_3$ is A, $X_5$ is A, $X_6$ is G and $X_7$ is D, $X_8$ is not P.

2. The composition according to claim 1, wherein the radiosensitizing peptide sequence is a following amino acid sequence:

CKSKSRRSC. (SEQ ID NO. 1)

3. The composition according to claim 1, wherein the synthetic peptide has a membrane-permeable peptide sequence on a N-terminal side or C-terminal side of the radiosensitizing peptide sequence.

4. The composition according to claim 3, wherein the synthetic peptide has for the membrane-permeable peptide sequence a following amino acid sequence:

KKRTLRKNDRKKR. (SEQ ID NO. 2)

5. The composition according to claim 1, wherein a total number of amino acid residues that constitute the synthetic peptide is 30 or less.

6. The composition according to claim 1, wherein the tumor cells are any of tumor cells constituting prostate cancer, cervical cancer, breast cancer, gallbladder cancer, pancreatic cancer, colon cancer, rectal cancer, kidney cancer, lung cancer, esophageal cancer, laryngeal cancer, stomach cancer, melanoma, mesothelioma or sarcoma.

7. The composition according to claim 1, wherein the radiation used in the radiation therapy is any of X-rays or electromagnetic waves having a wavelength shorter than that of X-rays, a proton beam, or a heavy particle beam using ions having a mass equal to or greater than helium.

8. The composition according to claim 1, wherein the radiation used in the radiation therapy is X-rays.

9. A method for inhibiting proliferation of at least one type of tumor cell, the method comprising:
supplying a synthetic peptide that increases radiosensitivity of target tumor cells to target cells; and
irradiating the cells with radiation after supplying the peptide, wherein,
the synthetic peptide is a peptide having a radiosensitizing peptide sequence including a following amino acid sequence:

$CX_2X_3KX_5X_6X_7X_8C$ wherein
$X_2$ represents K or R,
$X_3$ represents S or A,
$X_5$ represents S or A,
$X_6$ represents R or G,
$X_7$ represents R or D and
$X_8$ represents S or P, with the proviso that when $X_2$ is R, $X_3$ is A, $X_5$ is A, $X_6$ is G and $X_7$ is D, $X_8$ is not P, and
the radiation is any of X-rays or electromagnetic waves having a wavelength shorter than that of X-rays, a proton beam, or a heavy particle beam using ions having a mass equal to or greater than helium.

10. The method for inhibiting proliferation of tumor cells according to claim 9, wherein the radiosensitizing peptide sequence is a following amino acid sequence:

CKSKSRRSC. (SEQ ID NO. 1)

11. The method for inhibiting proliferation of tumor cells according to claim 9, wherein the radiation is X-rays.

12. A tumor treatment method, comprising
administering a synthetic peptide that increases radiosensitivity of target tumor cells to a patient, and
irradiating an affected area of the tumor with radiation, wherein,
the synthetic peptide is a peptide having a radiosensitizing peptide sequence including a following amino acid sequence:

$CX_2X_3KX_5X_6X_7X_8C$ wherein
$X_2$ represents K or R,
$X_3$ represents S or A,
$X_5$ represents S or A,
$X_6$ represents R or G,
$X_7$ represents R or D and
$X_8$ represents S or P, with the proviso that when $X_2$ is R, $X_3$ is A, $X_5$ is A, $X_6$ is G and $X_7$ is D, $X_8$ is not P, and
the radiation is any of X-rays or electromagnetic waves having a wavelength shorter than that of X-rays, a proton beam, or a heavy particle beam using ions having a mass equal to or greater than helium.

* * * * *

```
SEQUENCE LISTING

<160> NUMBER OF SEQ ID NOS: 8

<210> SEQ ID NO 1
<211> LENGTH: 9
<212> TYPE: PRT
<213> ORGANISM: Artificial sequence
<220> FEATURE:
<223> OTHER INFORMATION: Synthetic peptide

<400> SEQUENCE: 1

Cys Lys Ser Lys Ser Arg Arg Ser Cys
1               5

<210> SEQ ID NO 2
<211> LENGTH: 13
<212> TYPE: PRT
<213> ORGANISM: Artificial sequence
<220> FEATURE:
<223> OTHER INFORMATION: Synthetic peptide

<400> SEQUENCE: 2

Lys Lys Arg Thr Leu Arg Lys Asn Asp Arg Lys Lys Arg
1               5                   10

<210> SEQ ID NO 3
<211> LENGTH: 8
<212> TYPE: PRT
<213> ORGANISM: Artificial sequence
<220> FEATURE:
<223> OTHER INFORMATION: Synthetic peptide

<400> SEQUENCE: 3

Trp Arg Arg Gln Ala Arg Phe Lys
1               5

<210> SEQ ID NO 4
<211> LENGTH: 11
<212> TYPE: PRT
<213> ORGANISM: Artificial sequence
<220> FEATURE:
<223> OTHER INFORMATION: Synthetic peptide

<400> SEQUENCE: 4

Tyr Gly Arg Lys Lys Arg Arg Gln Arg Arg Arg
1               5                   10

<210> SEQ ID NO 5
```

```
<211> LENGTH: 11
<212> TYPE: PRT
<213> ORGANISM: Artificial sequence
<220> FEATURE:
<223> OTHER INFORMATION: Synthetic peptide

<400> SEQUENCE: 5

Tyr Ala Arg Ala Ala Ala Arg Gln Ala Arg Ala
1               5                   10

<210> SEQ ID NO 6
<211> LENGTH: 16
<212> TYPE: PRT
<213> ORGANISM: Artificial sequence
<220> FEATURE:
<223> OTHER INFORMATION: Synthetic peptide

<400> SEQUENCE: 6

Arg Gln Ile Lys Ile Trp Phe Gln Asn Arg Arg Met Lys Trp Lys Lys
1               5                   10                  15

<210> SEQ ID NO 7
<211> LENGTH: 23
<212> TYPE: PRT
<213> ORGANISM: Artificial sequence
<220> FEATURE:
<223> OTHER INFORMATION: Synthetic peptide

<400> SEQUENCE: 7

Cys Lys Ser Lys Ser Arg Arg Ser Cys Gly Lys Lys Arg Thr Leu Arg
1               5                   10                  15

Lys Asn Asp Arg Lys Lys Arg
            20

<210> SEQ ID NO 8
<211> LENGTH: 9
<212> TYPE: PRT
<213> ORGANISM: Artificial sequence
<220> FEATURE:
<223> OTHER INFORMATION: Synthetic peptide

<400> SEQUENCE: 8

Cys Arg Ala Lys Ala Gly Asp Pro Cys
1               5
```